(12) United States Patent
Honkanen et al.

(10) Patent No.: US 8,246,760 B2
(45) Date of Patent: Aug. 21, 2012

(54) CONTINUAL FLOW PIN WASHER

(75) Inventors: Peter Honkanen, Concord, MA (US);
Albert Bukys, Lexington, MA (US);
Dave Bradbury, Center Barnstead, NH (US)

(73) Assignee: Aushon Biosystems, Billerica, MA (US)

( * ) Notice: Subject to any disclaimer, the term of this patent is extended or adjusted under 35 U.S.C. 154(b) by 0 days.

(21) Appl. No.: 13/232,593

(22) Filed: Sep. 14, 2011

(65) Prior Publication Data

US 2012/0000493 A1     Jan. 5, 2012

Related U.S. Application Data

(63) Continuation of application No. 12/252,487, filed on Oct. 16, 2008, now Pat. No. 8,020,571.

(60) Provisional application No. 60/980,628, filed on Oct. 17, 2007.

(51) Int. Cl.
*B08B 3/00* (2006.01)

(52) U.S. Cl. .............. 134/34; 134/22.18; 134/166 R; 422/501; 422/510

(58) Field of Classification Search ............ 134/22.18, 134/25.4, 34, 54, 102.2, 118, 140, 154, 166 R, 134/187; 422/501, 510, 527, 551; 436/43, 436/49, 54
See application file for complete search history.

(56) References Cited

U.S. PATENT DOCUMENTS

| | | | |
|---|---|---|---|
| 4,730,631 A | | 3/1988 | Schwartz |
| 5,160,378 A | | 11/1992 | Tuunanen et al. |
| 5,186,194 A | * | 2/1993 | Kitajima ................. 134/154 |
| 5,279,794 A | * | 1/1994 | Sasao ...................... 422/510 |
| 5,474,744 A | * | 12/1995 | Lerch ...................... 422/510 |
| 5,650,122 A | * | 7/1997 | Harris et al. ............ 422/81 |
| 5,803,987 A | * | 9/1998 | DeWitt et al. ........... 134/25.4 |
| 5,976,470 A | * | 11/1999 | Maiefski et al. ........ 422/501 |
| 6,170,494 B1 | * | 1/2001 | Marinaro et al. ........ 134/22.18 |
| 6,325,080 B1 | | 12/2001 | Held et al. |
| 6,418,946 B1 | * | 7/2002 | Marinaro et al. ........ 134/166 R |
| 6,475,444 B1 | * | 11/2002 | Zimmermann et al. ... 422/551 |
| 2002/0059945 A1 | | 5/2002 | Maiefski et al. |
| 2002/0106813 A1 | | 8/2002 | Smith et al. |
| 2004/0129299 A1 | | 7/2004 | Kocherlakota et al. |
| 2004/0266015 A1 | | 12/2004 | Favuzzi et al. |
| 2005/0136534 A1 | | 6/2005 | Austin et al. |

OTHER PUBLICATIONS

International Search Report and Written Opinion issued for PCT/US2008/080122, dated Dec. 12, 2008.

* cited by examiner

*Primary Examiner* — Michael Barr
*Assistant Examiner* — Benjamin Osterhout
(74) *Attorney, Agent, or Firm* — Wilmer Cutler Pickering Hale & Dorr LLP

(57) ABSTRACT

A multi-chambered deposition pin wash station is provided. The wash station includes a lower chamber and an upper drain basin connected by a plurality of wash tubes. Cleaning fluid is provided to the lower chamber and passes through the cleaning tubes into the upper drain basin. The cleaning tubes are adapted to clean a single deposition pin with a single tube per wash cycle.

15 Claims, 11 Drawing Sheets

CONTINUAL FLOW PIN WASHER

CROSS-REFERENCE TO RELATED APPLICATIONS

This application is a continuation of U.S. application Ser. No. 12/252,487, filed Oct. 16, 2008, which claims the benefit under 35 U.S.C. §119(e) to U.S. Provisional Patent Application No. 60/980,628, entitled Continual Flow Pin Washer, filed Oct. 17, 2007. The entire contents of the above-identified applications are incorporated by reference herein.

BACKGROUND

1. Field of Inventions

The inventions relate to cleaning deposition pins, and, more specifically, cleaning deposition pins while minimizing cross-contamination between the pins and minimizing the volume of cleaning fluid required.

2. Description of Related Art

Systems and method are known for cleaning implements used for the deposition of fluid, semi-fluid or solid samples of biological or chemical materials, for example in microarray spotting, plate-to-plate transfer, or colony picking equipment. Examples of such implements are solid pins, quill-type pins, capillary tubes, or ink jet tubes. For simplicity, all of these implements will be referred to as pins.

Washing of deposition pins can be achieved through several mechanisms. All pins being used could be lowered into a bath of cleaning solution and agitated, either by agitation of the fluid or by motion of the pins themselves. Agitation could be implemented by creating a moving fluid flow, a re-circulating fluid flow, or sonication.

In a single common bath, material removed from one pin could be re-deposited on and contaminate adjacent pins. This contamination can be mitigated by using large bath volumes or by incorporating a fluid flow away from the pin surfaces to be cleaned. However, in such a system, the volume of cleaning fluid needed to maintain a supply of uncontaminated fluid at the cleaning surfaces can be excessive, with the added complications of storage or transportation of fresh fluid or waste fluid in the system.

High frequency coupling of energy (sonication, ultrasonics, megasonics, etc.) to aid the cleaning process can be implemented, but adds cost and complexity to implement the drive elements and proper mechanical design to couple the energy on all of the targeted surfaces to be cleaned.

SUMMARY OF THE INVENTION

The invention provided methods of and systems for cleaning deposition pins.

Under an aspect of the invention, a pin wash station includes a lower chamber, a drain basin, a plurality of cleaning tubes, and a vent tube. Each cleaning tube has an inlet end and an outlet end. Each tube inlet end is in fluid communication with the lower chamber. The terminus of all tube inlet ends are below a substantially horizontal reference plane. Each tube outlet end is in fluid communication with the drain basin such that fluid that exits the outlet end of the tube passes into the drain basin. Each tube outlet end is adapted to receive at least a portion of a deposition pin. The vent tube has an inlet end and an outlet end. The inlet end is in fluid communication with the lower chamber. The terminus of the vent tube inlet end is above the level of the cleaning tube inlet ends relative to the substantially horizontal reference plane. The outlet end is in fluid communication with the drain basin.

Under another aspect of the invention, a system includes a plurality of pins adapted to deposit an array of material dots on a receiving surface and a pin wash station. The pin wash station includes a lower chamber, a drain basin, a plurality of cleaning tubes, and a vent tube. Each cleaning tube has an inlet end and an outlet end. Each tube inlet end is in fluid communication with the lower chamber. The terminus of all tube inlet ends is below a substantially horizontal reference plane. Each tube outlet end is in fluid communication with the drain basin. Each tube outlet end is adapted to receive one of the plurality of pins. The vent tube has an inlet end and an outlet end. The inlet end is in fluid communication with the lower chamber. The terminus of the vent tube inlet end is above the level of the cleaning tube inlet ends relative to the substantially horizontal reference plane. The outlet end is in fluid communication with the drain basin.

Under a further aspect of the invention, a method of cleaning a plurality of deposition pins in a cleaning system is provided. The cleaning system includes a lower chamber, a drain basin, and a plurality of cleaning tubes. Each cleaning tube has an inlet end and an outlet end. Each tube inlet end is in fluid communication with the lower chamber. Each tube outlet end is in fluid communication with the drain basin. Each tube outlet end is adapted to receive at least a portion of one of the deposition pins. The method includes providing a cleaning fluid into the lower chamber to a level above the outlet ends of each cleaning tube so that vapor within the lower chamber is displaced by the cleaning fluid. Cleaning fluid is provided past this point so that vapor remaining in the lower chamber is compressed and the cleaning fluid flows upward through the cleaning tubes. The method also includes disposing at least a portion of a single one of the deposition pins in the tube outlet end of one of the cleaning tubes while the cleaning fluid flows through the cleaning tubes so that the pin is washed within the tube.

Under yet another aspect of the invention, the tube outlet ends are arranged in rows and the method further includes disposing a first row of deposition pins in a row of tube outlet ends; each tube outlet end of the row receiving no more than one deposition pin of the first row of deposition pins. The method also includes removing the first row of deposition pins from the row of tube outlet ends and, subsequent to removing the first row of deposition pins from the row of tube outlet ends, disposing a second row of deposition pins in the row of tube outlet ends. Each tube outlet end of the row receives no more than one deposition pin of the second row of deposition pins.

Under still another aspect of the invention, a plurality of pins are disposed in a plurality of tubes on a one-for-one basis. The tube outlet ends are above a level of cleaning fluid such that each of the plurality of pins is washed within a respective cleaning tube. The cleaning fluid passes each tube and exits at outlet ends such that the fluid that cleans a first pin is drained and does not come into fluid contact with a second pin.

BRIEF DESCRIPTION OF THE SEVERAL VIEWS OF THE DRAWINGS

For a more complete understanding of various embodiments of the present inventions, reference is now made to the following descriptions taken in connection with the accompanying drawings in which:

FIGS. 10a-10c, is a side view of an arrangement of cleaning tubes for an interlaced cleaning system.

DETAILED DESCRIPTION

Embodiments of the inventions include methods of and systems for cleaning deposition pins. Deposition pins are used to deposit small quantities of fluid, semi-fluid, or solid samples of biological or chemical materials. They are usually arranged in an array. Typically, it is a regular two-dimensional rectangular array (e.g., a 48 pin array is typically a 4×12 arrangement of pins), but an array could be one-dimensional, have an irregular pattern, or be a single pin. Deposition pins are relatively small, and can be approximately 43-50 mm in overall length, have an extraction depth of 10-16 mm, a diameter ranging between 3.2-1.9 mm along the length of the pin, and a tip diameter between 85-355 μm. However, deposition pins can have dimensions that are larger or smaller than these dimensions and still be used with embodiments of the inventions. Embodiments of the inventions can be used with automated microarray printing systems, such as the one disclosed in U.S. patent application Ser. No. 10/972,792, entitled "Apparatus and Method For Dispensing Fluid, Semi-Solid and Solid Samples", filed Oct. 25, 2004, incorporated by reference herein. This application describes a printing system that uses a printing head with multiple pins. However, as stated above, embodiments of the inventions can also be used to clean a single pin.

Figure 11:
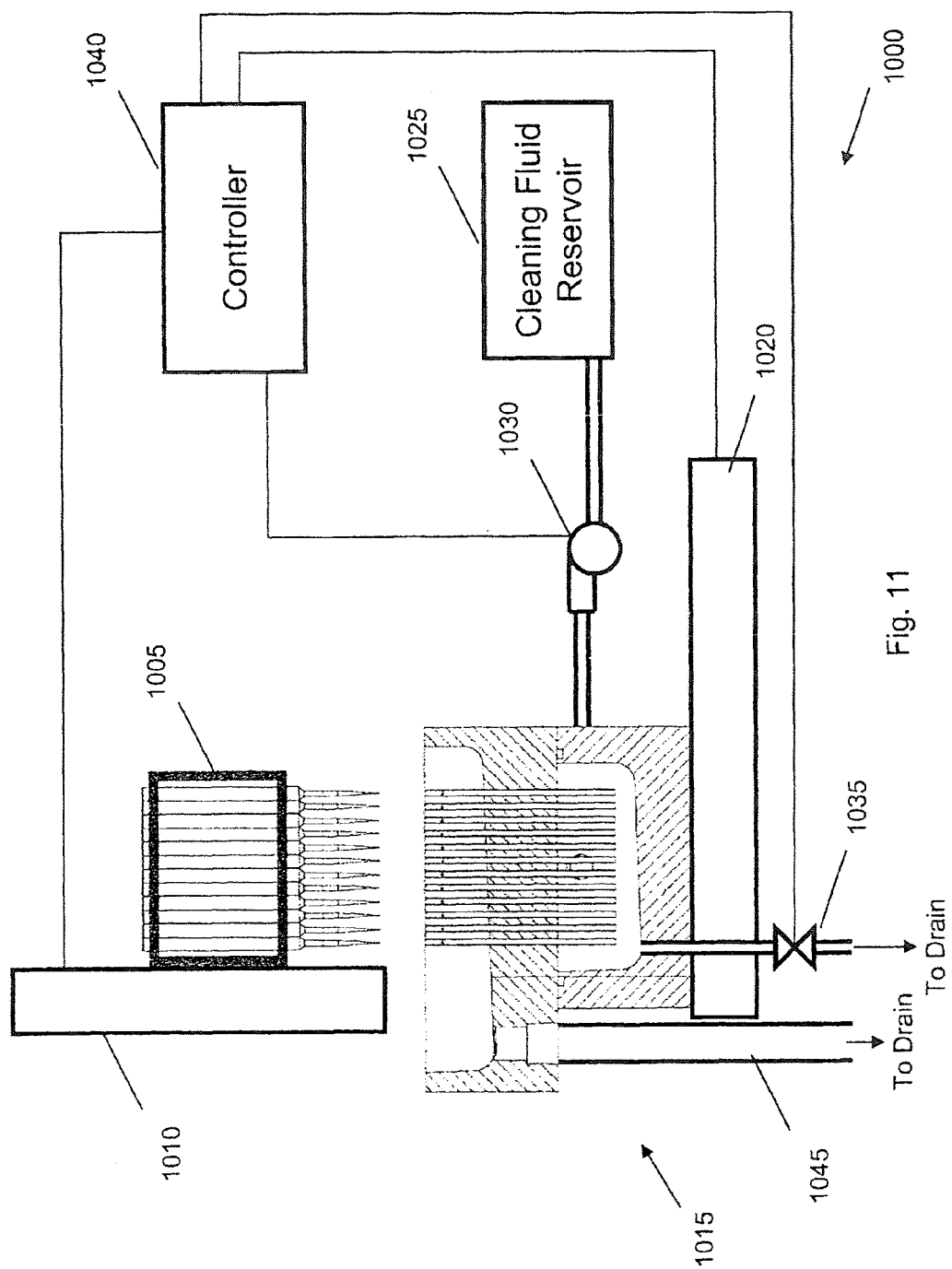
FIG. 11 is an overview of a pin washing system.

FIG. 11 is an overview of a pin washing system 1000. The washing system 1000 has a deposition pin array 1005 mounted on a pin array conveyor 1010. The pin array conveyor 1010 moves the pin array 1005 in the vertical direction. The washing system 1000 also includes a multi-chambered wash station 1015 mounted on a wash station conveyor 1020. The wash station 1015 is connected to a cleaning fluid reservoir 1025 via a fluid pump 1030 and to a drain by flow control valve 1035. The fluid pump 1030 and valve 1035 are controlled by a controller 1040. Likewise, the controller 1040 controls the position of the pin array 1005 on the pin array conveyor 1010 and the position of the wash station 1015 on the wash station conveyor 1020.

In some embodiments, the wash station conveyor 1020 moves the wash station 1015 in the horizontal plane to a position beneath the pin array 1005 that is to be washed. In other embodiments, the wash station 1015 remains in a fixed position. The pin array 1005 is lowered via the pin array conveyor 1010 such that the tips of the pins are washed in the wash station 1015, as described in greater detail below. Alternatively, the wash station 1015 can be connected to other conveyors to allow the pin array 1005 to remain motionless, while the wash station 1015 is moved as required to wash the pins of the pin array 1005. Likewise, the pin array 1005 can be connected to other conveyors to allow the wash station 1015 to remain motionless, while the pin array 1005 is moved as required to wash the pins of the pin array 1005.

The controller 1040 controls the fluid pump 1030 and valve 1035 remains closed to provide an appropriate flow of cleaning fluid to the wash station 1015. After one or more wash cycles are complete, valve 1035 is opened to drain any remaining cleaning fluid from the wash station 1015. The waste wash fluid exits the wash station 1015 through a drainage tube 1045. The drainage tube 1045 can convey used wash fluid to a reservoir or into a waste water system. In addition, the cleaning fluid reservoir 1025 can be an internal reservoir, an external reservoir, or can be connected to a continuous source of cleaning fluid.

Figure 1:
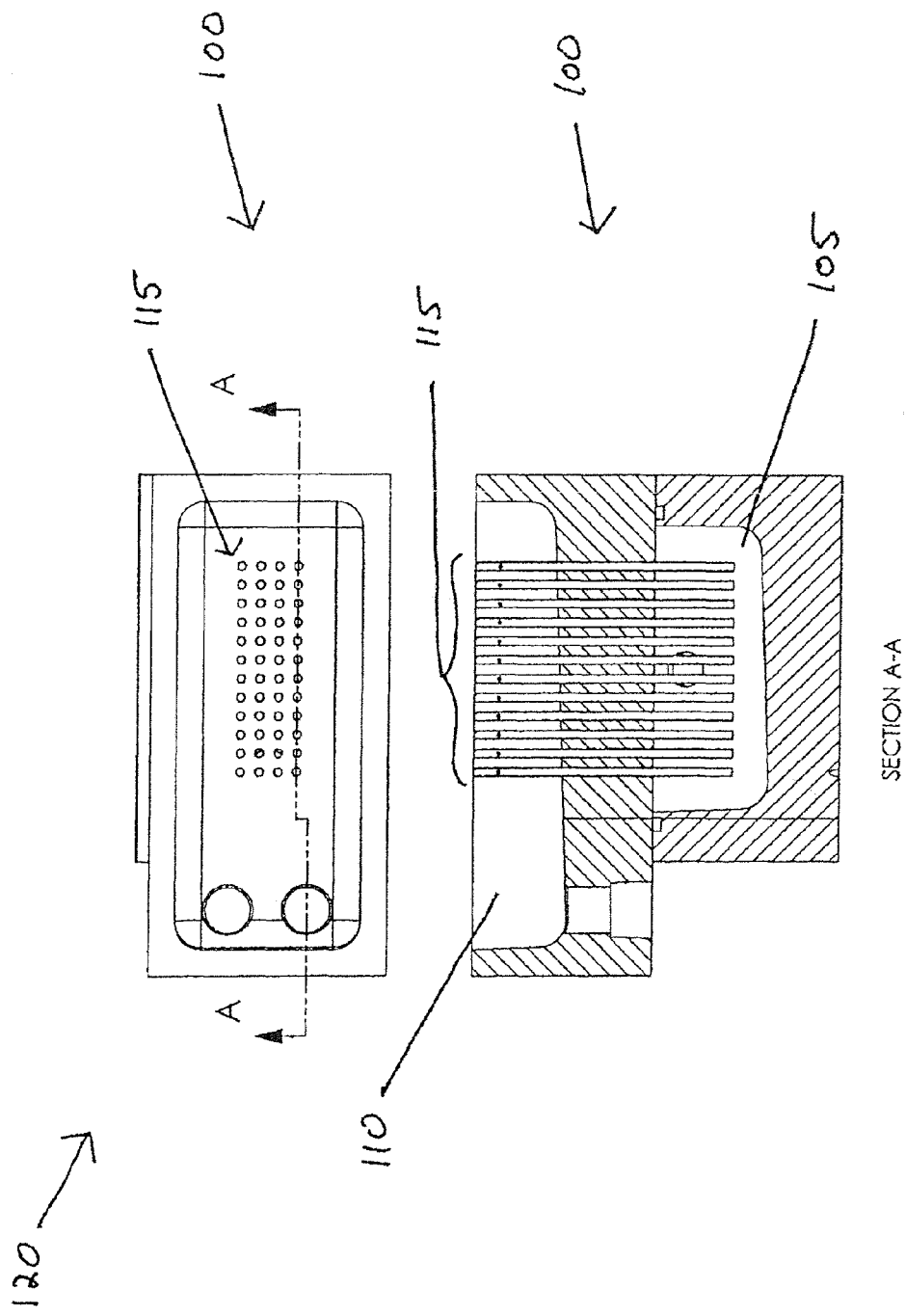
FIG. 1 is a top view and a cross-sectional side view of a multi-chambered wash station.

FIG. 1 is a top view and a cross-sectional side view of a multi-chambered wash station 100 for cleaning a two-dimensional array of deposition pins. While this embodiment is described as useful for cleaning an array of multiple pins, this embodiment, and others, may be used with a printing head having a single deposition pin. The multi-chambered wash station 100 has a lower chamber 105 and an upper drain basin 110, which are connected by one or more cleaning tubes 115. The cleaning tubes 115 are the primary fluid path between the two chambers. As shown in a top view 120 of the multi-chambered wash station 100, tubes 115 are arranged in multiple aligned rows (e.g., four rows of twelve tubes) to match a configuration of multiple pins in a printing array (not shown). As an alternative to separate tubes 115, machined features can be provided in the upper and lower chambers.

The lower chamber 105 is sealed to the drain basin 110 by one or more of a variety of known techniques around the mated surfaces of the lower chamber 105 and the drain basin 110. The tubes are sealed in the drain basin 110 such that the only path for air or liquid to pass from the lower chamber 105 to the drain basin 110 is through the tubes 115.

Figure 2:
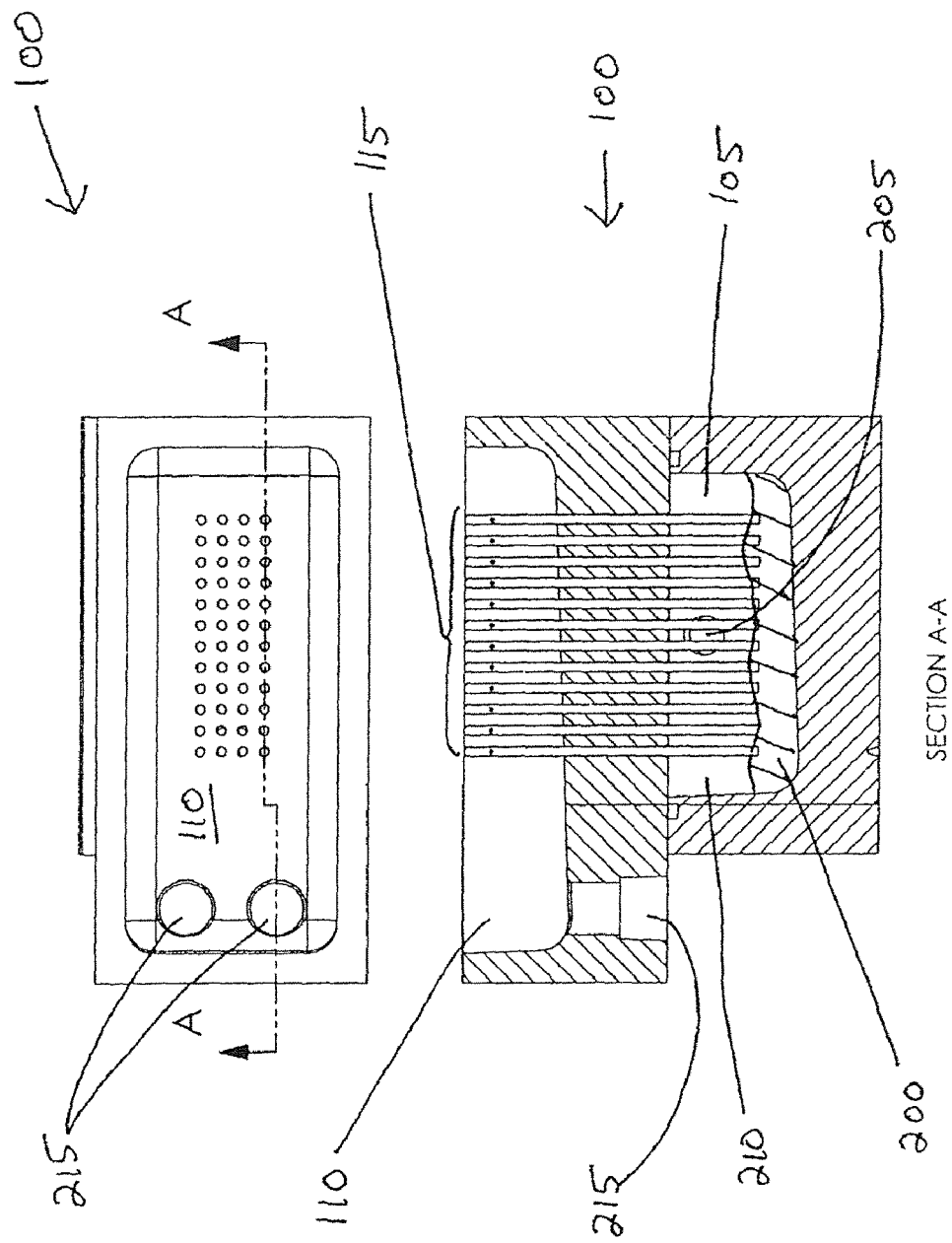
FIG. 2 is a top view and a cross-sectional side view of a multi-chambered wash station with cleaning fluid in the lower chamber.

FIG. 2 is a top view and a cross-sectional side view of the multi-chambered wash station 100 of FIG. 1 with cleaning fluid 200 in the lower chamber 105. Cleaning fluid 200 is pumped into the lower chamber 105 through cleaning fluid inlet 205 so that the fluid level rises and air 210 is displaced and pushed through the tubes 115. The fluid level 200 rises until it covers the bottom opening of the highest tube, measured relative to a reference plane that is parallel to the fluid level (e.g., the reference plane can be the substantially horizontal level of the fluid). Once the fluid level 200 reaches the highest tube, the air 210 no longer has a path to the upper drain basin 110. When this occurs, the rising fluid level 200 compresses the air 210 trapped at the top of the lower chamber 105 and a counter pressure is applied to the surface of the fluid 200 in the lower chamber 105. The pressure on the surface of the fluid 200 acts to push the fluid up each of the tubes 115.

The flow of cleaning fluid 200 from the lower chamber 105 up the tubes 115 and into the drain basin 110 provides individual fountains for individual pins to be washed. One pin sits in each fountain to implement the washing action. The waste fluid then runs down the sides of the tubes 115 and ultimately drains from waste holes 215 in the upper drain basin. Although the tubes 115 wash one pin at a time during a single wash cycle, each tube 115 need not be occupied by a pin during a particular cycle. Thus, the number of tubes 115 can exceed the number of pins in a particular printing array to be washed. Likewise, a printing array may have more pins that the number of tubes 115 of a particular wash station. In such a scenario, all pins of the array can be cleaned by the wash station by cleaning different pins of the array in sequential wash cycles, as described in greater detail below.

In one implementation of the multi-chambered wash station 100, all tubes 115 have the same inner diameter. Because all tubes 115 share the same fluid reservoir, i.e., the lower chamber 105, the fluid pressure per unit area is equal at the bottom of each tube 115 and equal fluid flow is generated in all of the tubes 115. This is an efficient and inexpensive means for creating a multiplicity of equal flow rates for washing.

Figure 3:
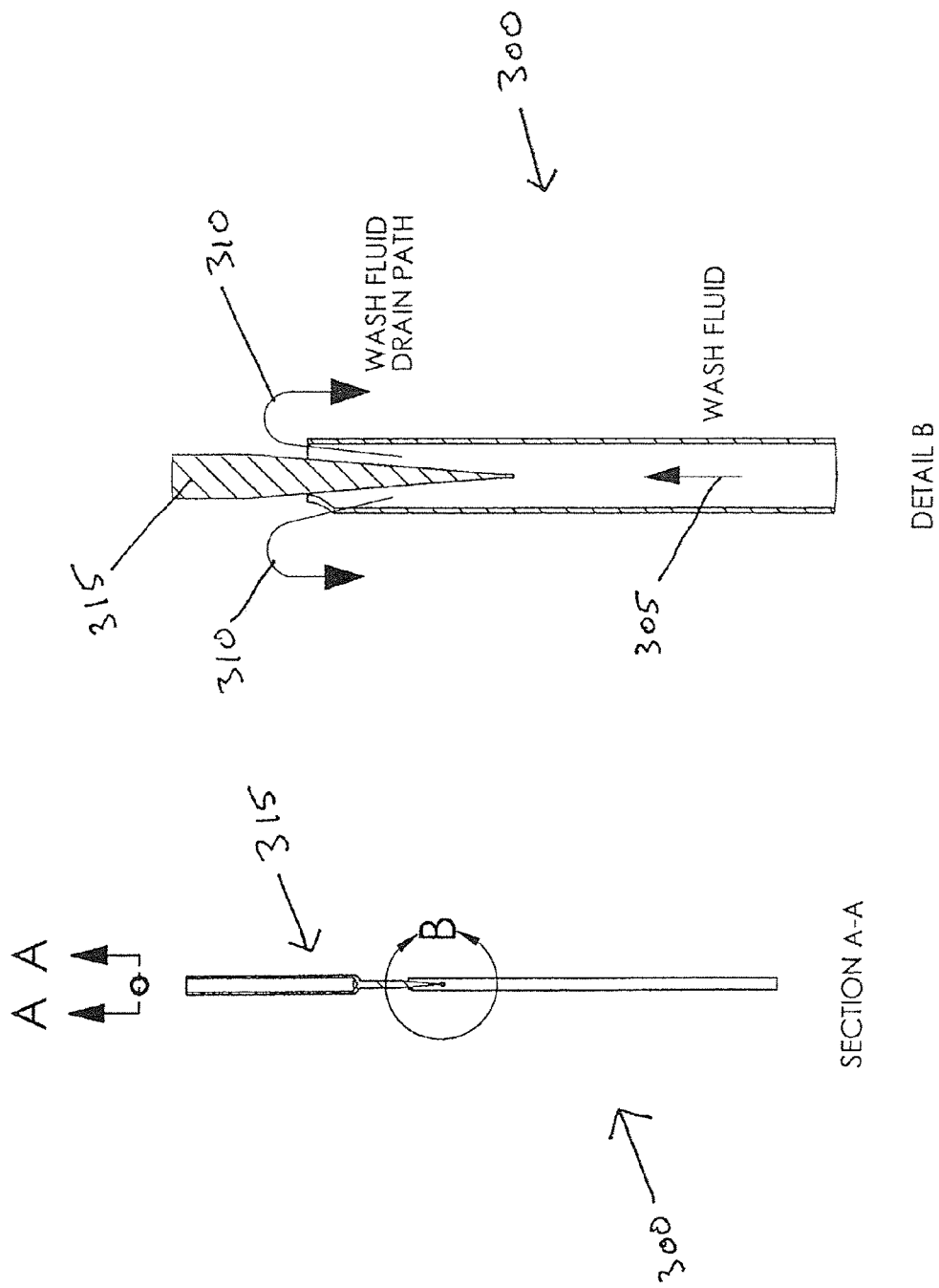
FIG. 3 is a cross-sectional side view of a single cleaning tube and a single printing pin.

FIG. 3 is a cross-sectional side view of a single cleaning tube 300 and a single printing pin 315. As shown in FIG. 3, a flow 305 of cleaning fluid, i.e., wash fluid, up the tube 300 provides an individual fountain 310 for an individual pin 315 to be washed. In this manner, each pin has an independent supply of uncontaminated wash fluid. Because the geometry of the tubes can be made to closely match the needs of the pins to be washed, the tubes can be designed to increase or maximize the delivery of uncontaminated fluid while reducing or minimizing the quantity of fluid used. Flow of uncontaminated material is delivered precisely to the surfaces to be cleaned, thus reducing the amount of fluid otherwise needed.

In at least one implementation of the multi-chambered wash station 100 of FIGS. 1 and 2, the placement of the tubes 115 (as best illustrated by the top view 120 of FIG. 1) is such that there is sufficient spacing between the tubes 115 so that all waste fluid runs down the sides of the tubes 115 without mixing with either the waste fluids or wash fluids of adjacent tubes. In this manner, the possibility of tube-to-tube cross contamination is reduced, allowing for lower fluid flow rates to be used than would be possible without this drain path.

Figure 4:
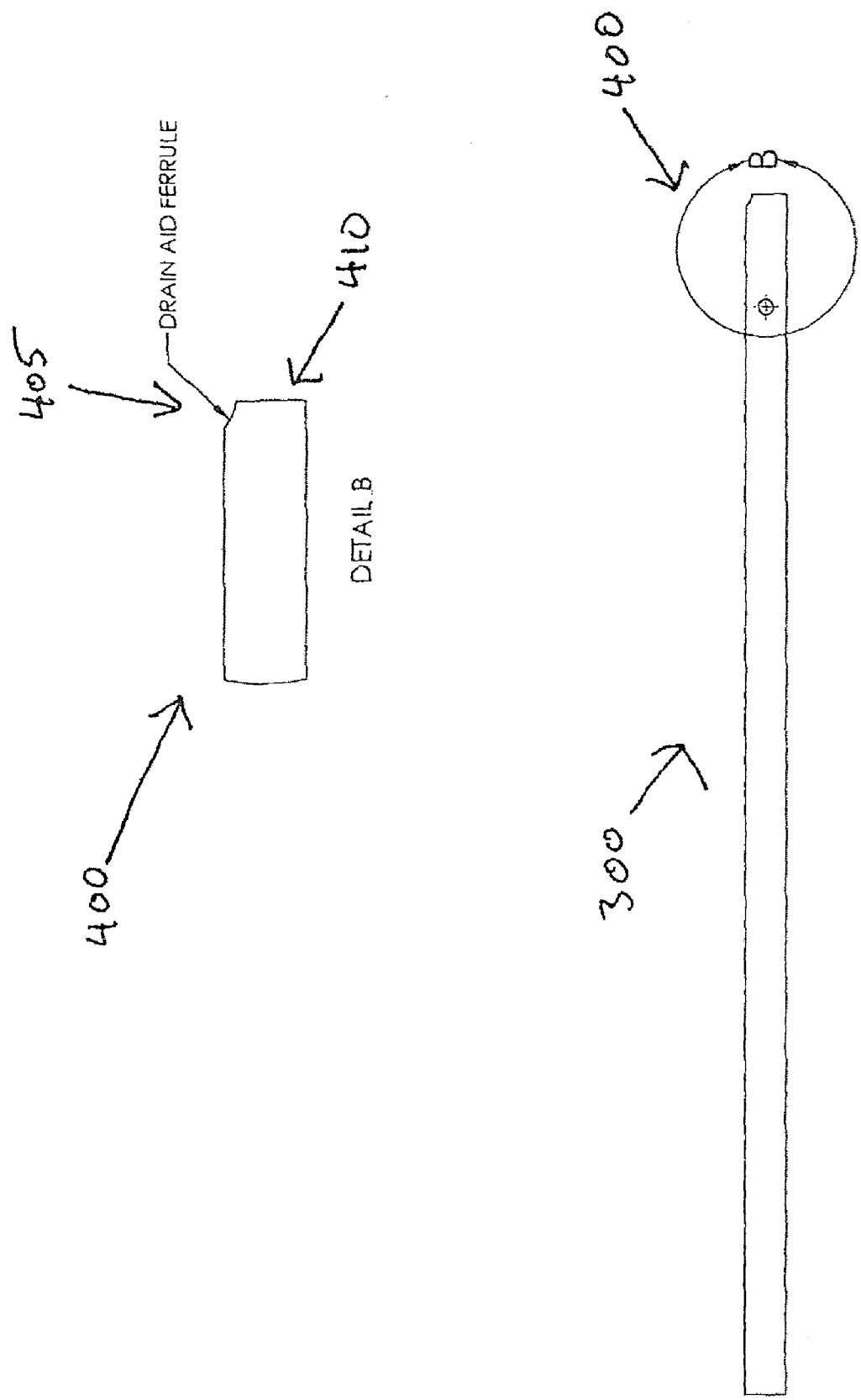
FIG. 4 is a side view of a drain end of a single cleaning tube.

In some implementations, features are incorporated into the tubes 115 to aid waste fluid flow away from the pins. Without these features, the cleaning fluid can form a spherical droplet at the top of an otherwise unmodified tube because of the surface tension of the cleaning fluid and the small size of the tubes 115. FIG. 4 is a side view of a drain end 400 of the single cleaning tube 300 of FIG. 3 incorporating a drain feature. Such features can be, but are not limited to, a notch 405 in an upper lip 410 of the tube 300. In addition, the surface finish of the tube 300 can be manipulated to work against the cleaning fluid's surface tension and enhance flow down the outside of the tube. Examples of such treatments are bead blasting and grit blasting. Also, chemical deposition can be applied to similarly enhance the hydrophilic properties of the tubes 115. Likewise, a chemical deposition can be applied to enhance the hydrophobic properties of the tubes 115, depending on the cleaning fluid employed. These treatments need not be applied uniformly, but could be applied over controlled paths to enhance waste fluid flow along desired paths. In some implementations, the features and treatments incorporated into the tubes can be preferentially oriented such that waste fluid from one tube is directed toward the controlled waste path of an adjacent tube, thus allowing closer spacing between tubes without mixing adjacent tube wash and waste fluids.

Figure 5:
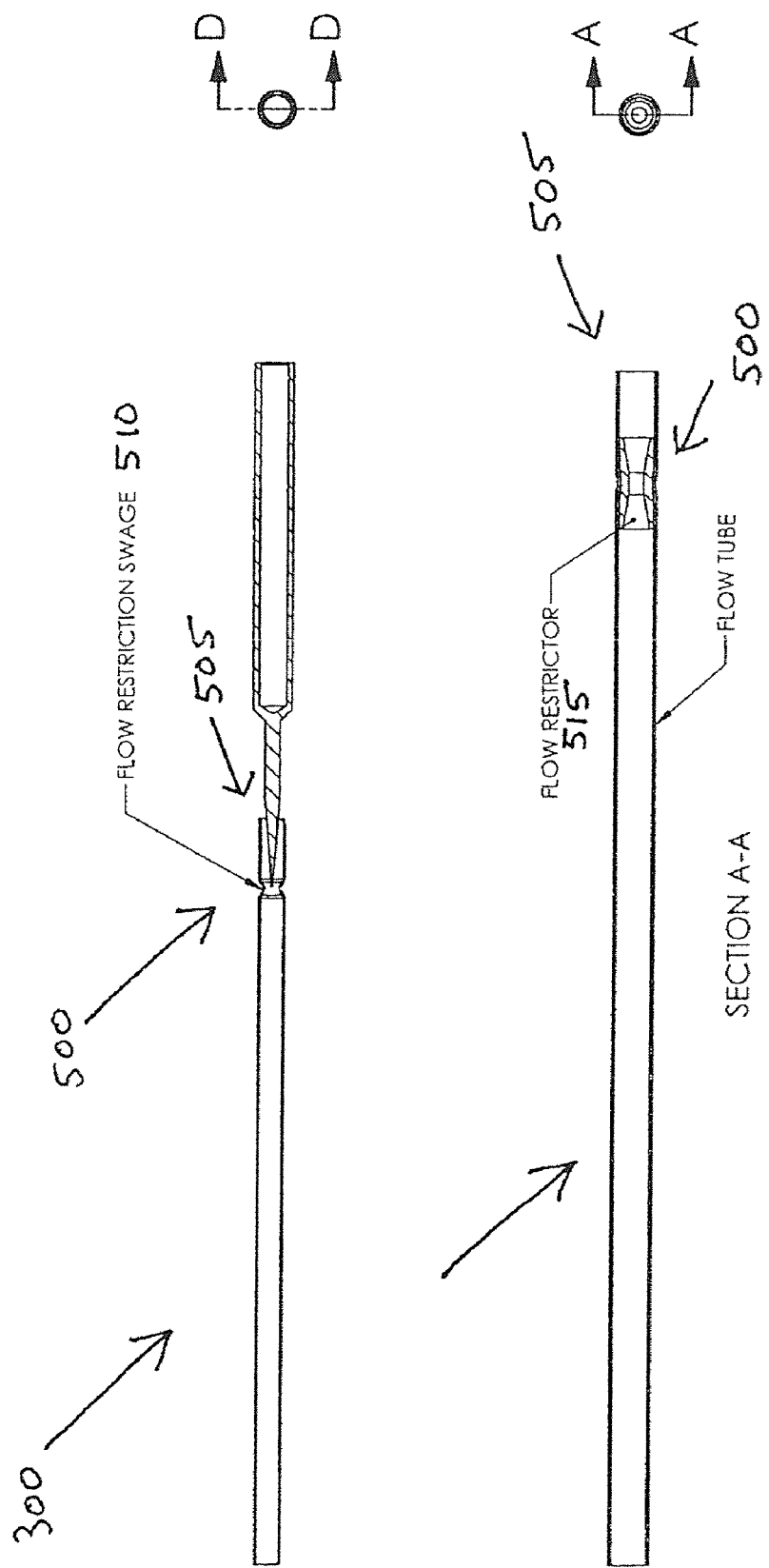
FIG. 5 is a cross-sectional side view of a cleaning tube with a flow restriction feature in the fluid exit end of the tube.

FIG. 5 is a cross-sectional side view of the cleaning tube 300 with a flow restriction feature 500 in a fluid exit end 505 of the tube 300. Two examples of the flow restriction feature are shown in FIG. 5. A first illustrative example is one in which the inner diameter of the tube is restricted by a swage 510 to create sections of higher fluid velocity at particular points along the length of the tube. The swage 510 is created by reducing the diameter of the tube 300. The swage 510 is located at a position along the tube 300 to correspond to the head of the pin to be cleaned. A second illustrative example is one in which a flow restrictor 515 is installed in the tube 300. The flow restrictor 515 narrows the tube's diameter at a position along the tube 300 to correspond to the head of the pin to be cleaned. In other embodiments, the flow restriction feature 500 is located to correspond to a position other than the head of the pin, e.g., in-front of or behind the head of the pin along the pin's length.

Although not illustrated, more complex features could be implemented within sections of the tube 300 to create rotating or agitated flow patterns in the areas of interest. For example, a swirl pattern could be etched on the inner surface of the tube or the surface of the flow restrictor 515 near the position that corresponds to the head of the pin to be cleaned. Similarly, a portion of the tube 300 or flow restrictor 515 could be roughened to cause turbulence in the region in which the head of the pin lies. The addition of rotation or turbulence in the cleaning fluid can aid in the cleaning of the pins.

Figure 6:
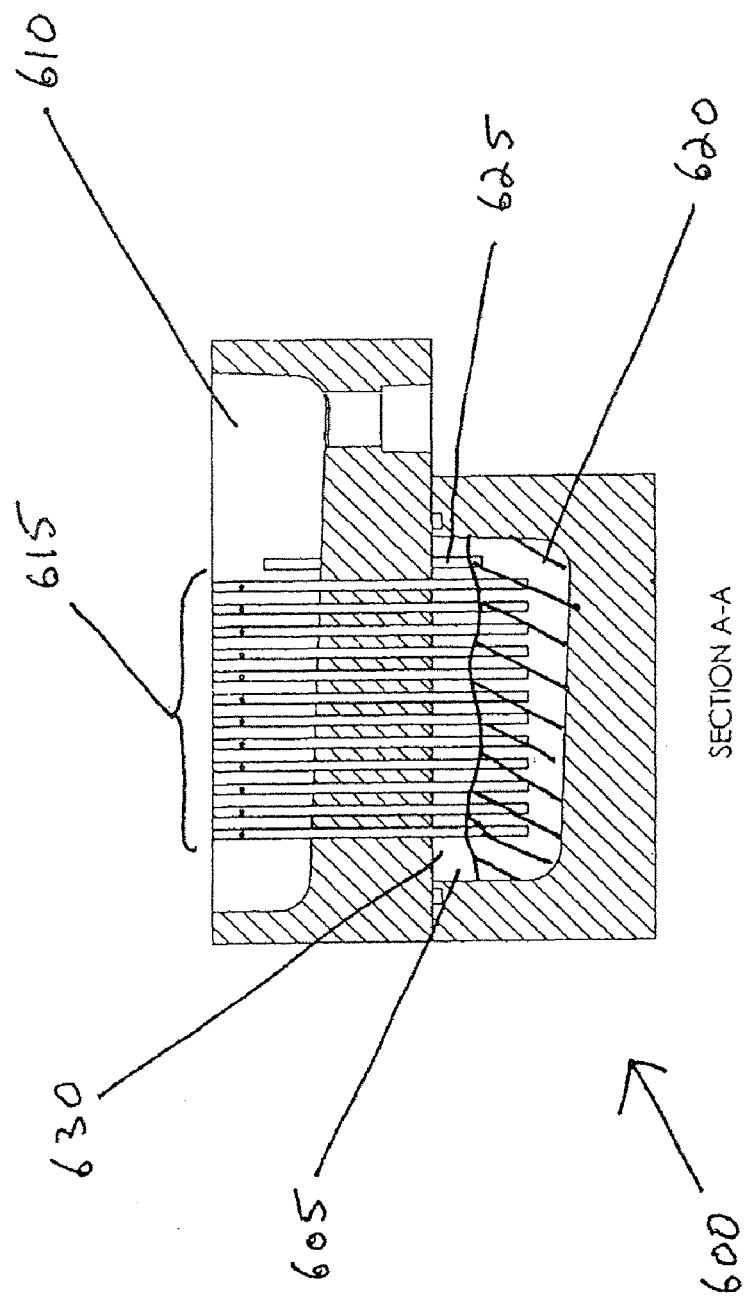
FIG. 6 is a cross-sectional side view of a multi-chambered wash station with a vent tube.

FIG. 6 is a cross-sectional side view of a multi-chambered wash station 600. Wash station 600 is similar to the implementation described above in conjunction with FIG. 1 and has a lower chamber 605, and drain basin 610, cleaning tubes 615, and holds a cleaning fluid 620 in the lower chamber 605. Wash station 600 also has a vent tube 625.

Transient fluctuations in the level of the cleaning fluid 620 in the lower chamber 605 can occur due to, e.g., variations in the pumped fluid flow rate, bubbles in the fluid source supply lines entering the lower chamber 605, and/or mechanical vibrations in the wash station structure. During such disturbances, the level of the cleaning fluid 620 can momentarily drop below the level of the one of the tubes 615. By exposing the bottom opening of one of the tubes 615, trapped air 630 escapes through the top of the tube, thereby depressurizing the lower chamber 605. This causes an interruption in the fluid flow through most, if not all, of the tubes 615. In addition, if the level of the fluid 620 varies rapidly around the inlet end of a working tube ("working tube" as used herein is a tube used to clean pins), then cleaning fluid can become entrained in the escaping air. This, in turn, can cause cleaning fluid to be sprayed out of the outlet end of the tube as the tube inlet is alternately covered and uncovered by the cleaning fluid. The sprayed cleaning fluid can cause contamination of pins and/or other equipment.

The inlet of the vent tube 625 is set at a height that is higher than any of the working tubes 615 (relative to the reference plane described above). In this way, the level of the cleaning fluid 620 in the lower chamber 605 is maintained above the inlet ends of the working tubes 615. Using the same principles described above, the height of the cleaning fluid 620 in the lower chamber 605 rises to the level set by the highest tube, which is now the vent tube 625. In the presence of fluid level fluctuations, the inlet ends of the working tubes 615 do not become uncovered, and therefore, the upward spray of cleaning fluid is avoided. The vent tube 625 can spray upward, but it is positioned such that it sprays in a non-detrimental direction.

Figure 7:
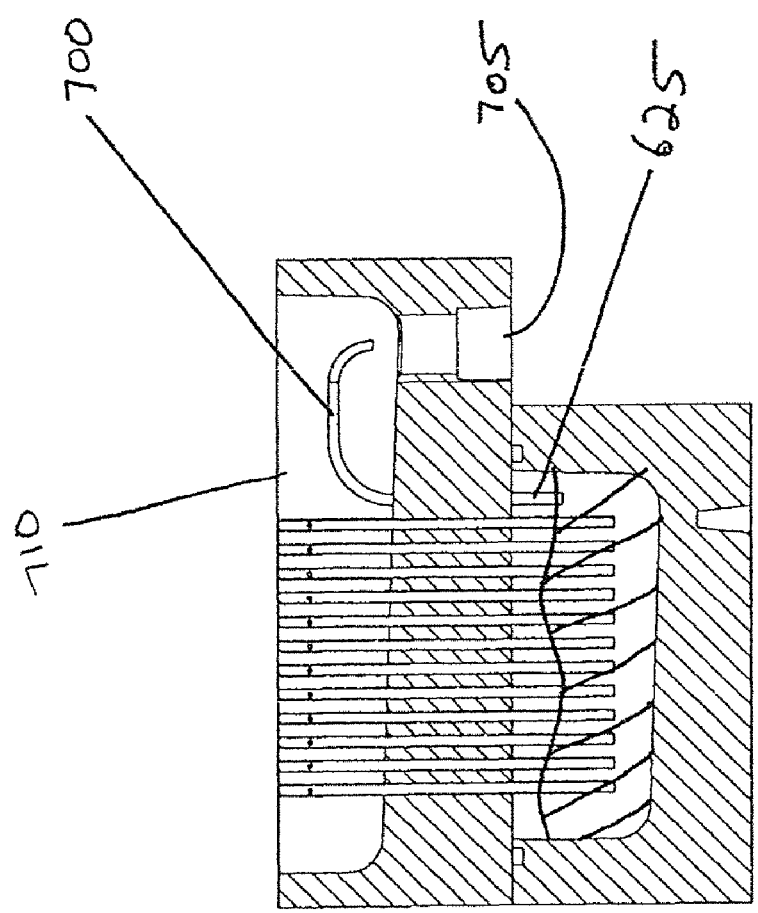
FIG. 7 is a cross-sectional side view of a multi-chambered wash station with a curved vent tube.

FIG. 7 is a cross-sectional side view of the multi-chambered wash station 600 of FIG. 6, in which the vent tube 625 is fitted with an optional curved outlet end 700. The curved outlet end 700 directs the potential spray away from the critical surfaces to be washed. The curved outlet end can be positioned to vent directly into one or more waste holes 705.

Figure 8:
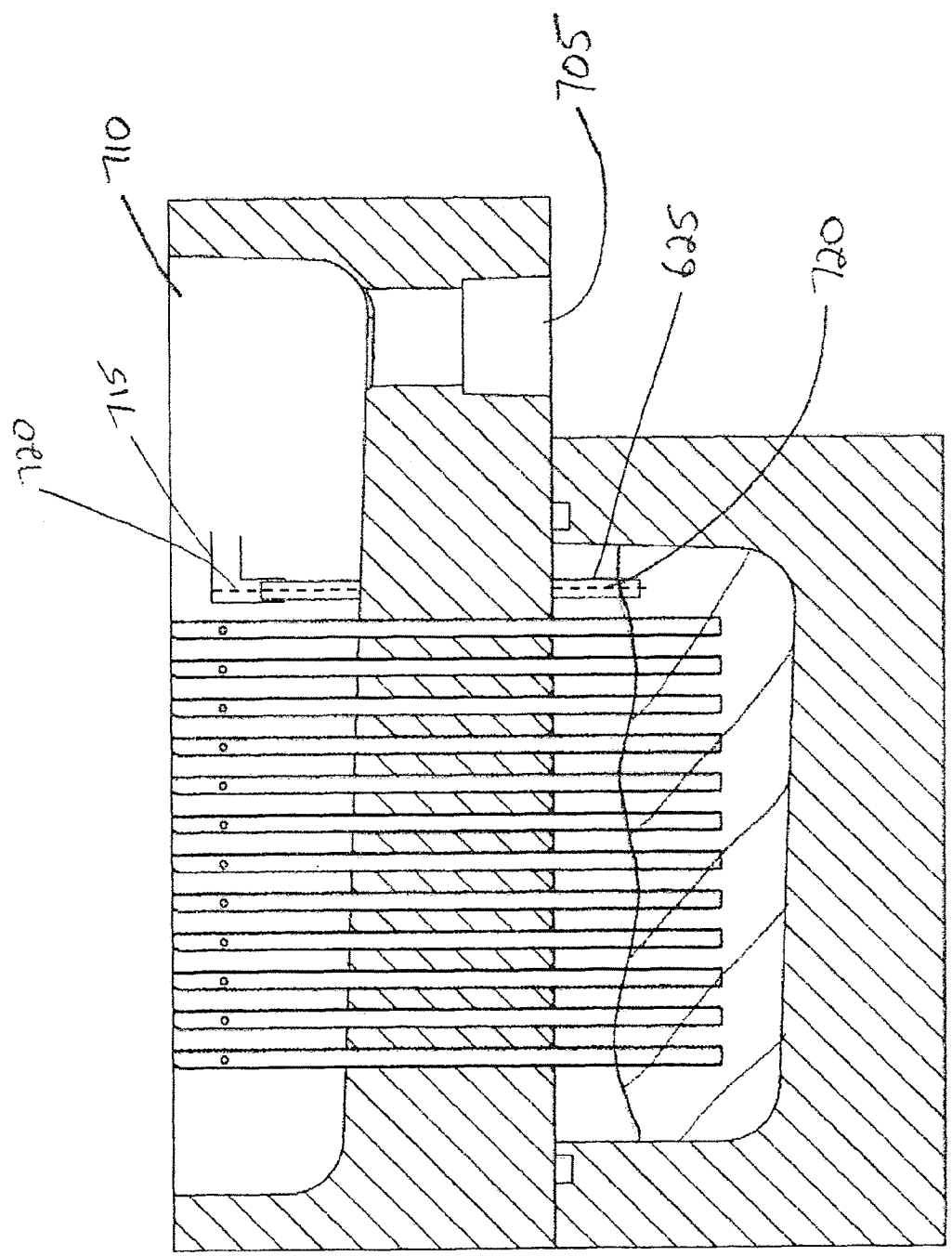
FIG. 8 is a cross-sectional side view of a multi-chambered wash station with a capped vent tube.

In addition, other methods can be employed to prevent cleaning fluid from spraying from the outlet of the vent tube 625. FIG. 8 is a cross-sectional side view of the multi-chambered wash station 600 of FIG. 6, in which the vent tube 625 includes a cap 715. The cap 715 directs potential spray sideways into drain basin 710. In addition, vent tube 625 can include a wire 720 that is disposed within and along the approximate central axis of vent tube 625. The wire 720 disrupts the surface tension of any fluid within vent tube 625. The wire 720 reduces the likelihood that fluid will clog the vent tube 625 after fluid has vented through the vent tube 625.

Figure 9:
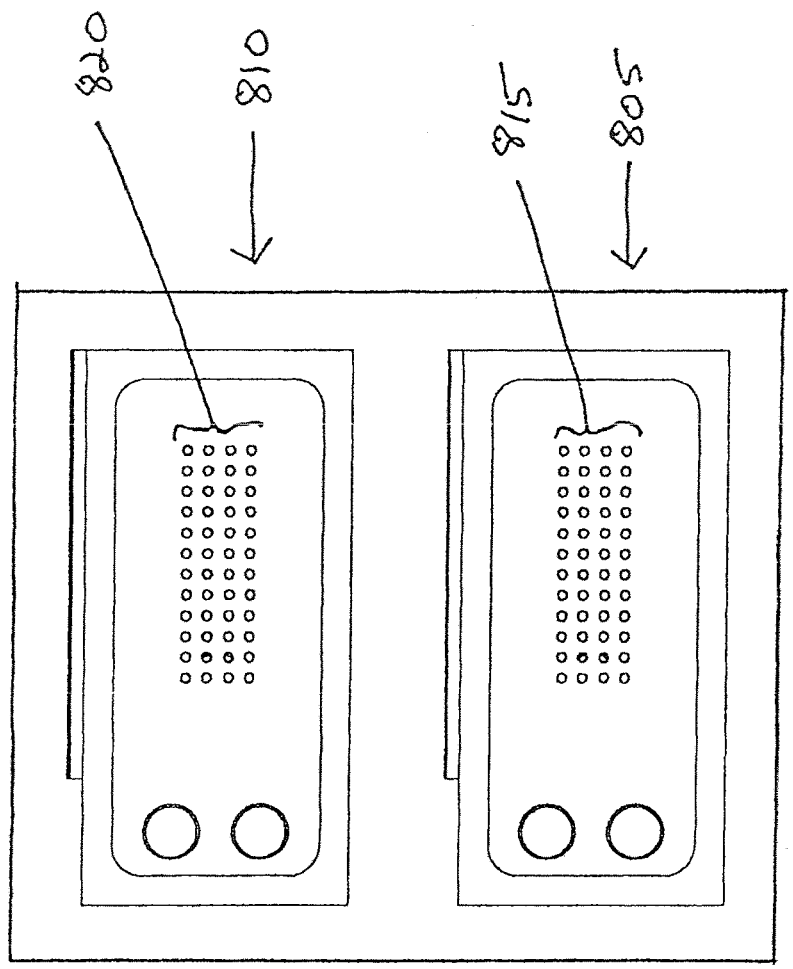
FIG. 9 is a top view of a multiple wash fluid cleaning system employing one or more multi-chambered wash stations.

FIG. 9 is a top view of a multiple wash fluid cleaning system 800 employing one or more multi-chambered wash stations. Any of the multi-chambered wash station implementations described above can be used in cleaning system 800.

In one embodiment the cleaning system 800 uses two multi-chambered wash stations. A first wash station 805 uses a first wash fluid, and a second wash station 810 uses a second wash fluid. Multiple fluid wash sequences are executed by alternatively entering working tubes 815 for the first wash station and then entering working tubes 820 for the second wash station. This multiplicity of fluids is not limited to two; nor is the sequence limited to alternating back and forth between the fluids. Cleaning system 800 can be implemented by motion of the pins as well as the described motion of the wash station.

In the embodiments and implementations set forth above, one working tube is described as being dedicated to a corresponding one pin to be cleaned. If, however, there are more pins in a given printing array to be cleaned than working tubes available, the wash stations and/or cleaning systems described above can incorporate motion, either of the tubes or of the pins, by an increment smaller than the spacing between working tubes.

Figure 10:
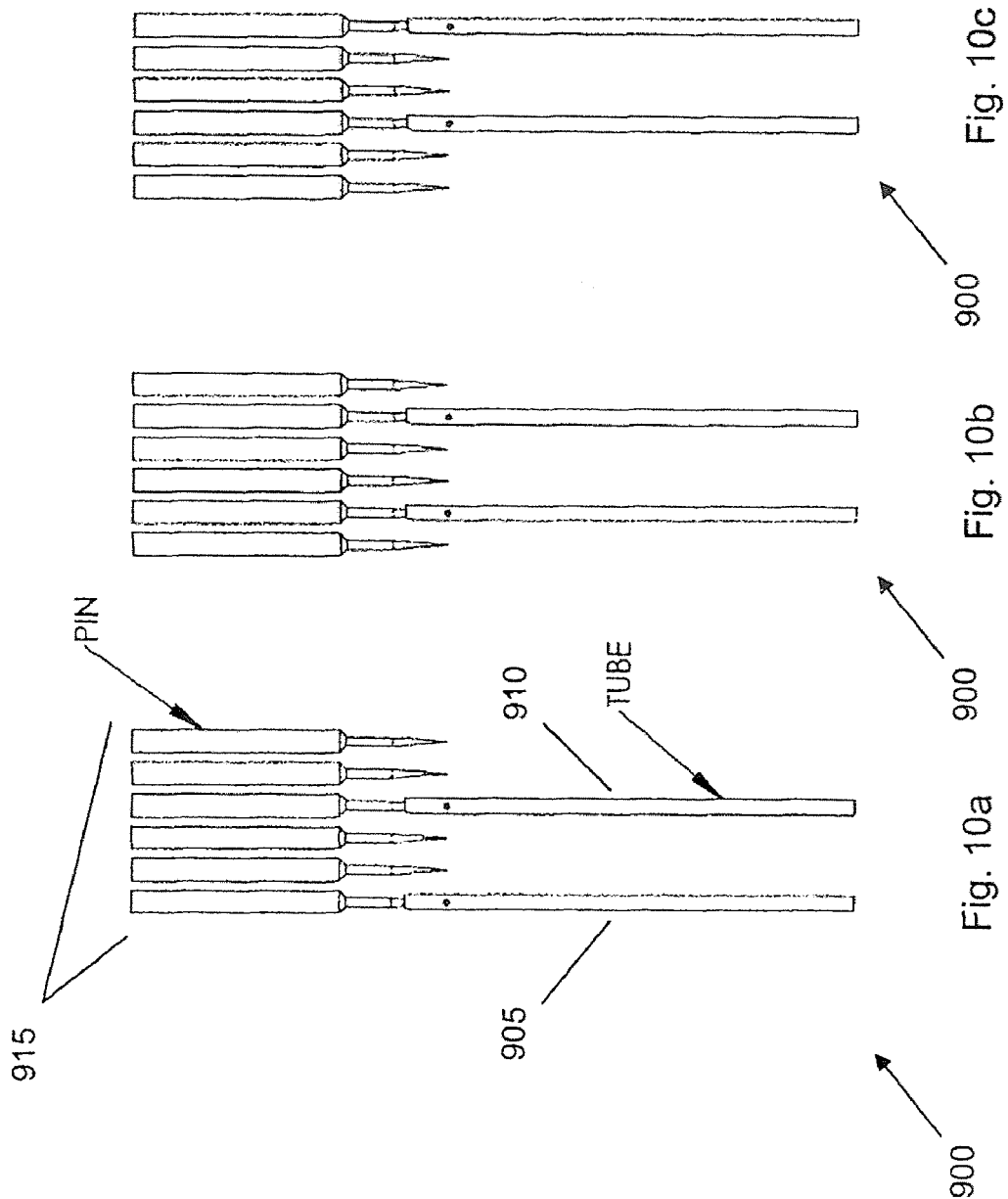
FIG. 10, which includes

FIG. 10, which includes FIGS. 10a-10c, is a side view of an arrangement of cleaning tubes for an interlaced cleaning system 900. Cleaning system 900 has a first row of working tubes 905 and a second row of working tubes 910. The spacing between the first and second rows of working tubes is greater than the spacing of rows of pins 915 in an array to be cleaned. All pins of the array can be cleaned using the interlaced cleaning sequence illustrated FIGS. 10a-10c.

The interlaced cleaning sequence provides for certain rows of pins to be cleaned in one wash cycle, while adjacent rows of pins are cleaned in the next cycle by moving either the pins or the cleaning tubes so as to mate the pins to the cleaning tubes. Working tubes can be set apart from each other by any integer increment (i.e., integer multiple) of the pin spacing. Such an embodiment is useful for use with, for example, printing arrays having a relatively large number of pins, e., 192 pins, 384 pins, 1536 pins, and greater.

As will be realized, the inventions are capable of other and different embodiments and its several details may be capable of modifications in various respects, all without departing from the invention as set out in the appended claims. Accordingly, the drawings and description are to be regarded as illustrative in nature and not in a restrictive of limiting sense, with the scope of the application being indicated in the claims.

What is claimed is:

1. A method of cleaning a plurality of deposition pins in a system with a lower chamber; a drain basin; a plurality of cleaning tubes, each cleaning tube having an inlet end and an outlet end, each tube inlet end being in fluid communication with the lower chamber, each tube outlet end being in fluid communication with the drain basin, and each tube outlet end adapted to receive at least a portion of one of the deposition pins; and a vent tube, the vent tube having an inlet end and an outlet end, the inlet end being disposed in and in fluid communication with the lower chamber, the terminus of the vent tube inlet end being above the level of the cleaning tube inlet ends relative to a substantially horizontal reference plane, and the outlet end being in direct fluid communication with the drain basin, the method comprising:
   providing a cleaning fluid into the lower chamber to a level above the outlet ends of each cleaning tube so that vapor within the lower chamber is displaced by the cleaning fluid, and continuing to provide the cleaning fluid so that vapor remaining in the lower chamber is compressed and the cleaning fluid flows upward through the cleaning tubes; and
   disposing at least a portion of a single one of the deposition pins in the tube outlet end of one of the cleaning tubes while the cleaning fluid flows through the cleaning tubes so that the pin is washed within the tube.

2. The method of claim 1, wherein at least one of the plurality of cleaning tubes includes a flow restriction feature and the disposing the deposition pin in the tube outlet end includes disposing a terminus of the deposition pin within the flow restriction feature.

3. The method of claim 2, wherein the flow restriction feature is a swage in at least a portion of the cleaning tube.

4. The method of claim 2, wherein the flow restriction feature includes a narrowing insert within at least a portion of the cleaning tube.

5. The method of claim 2, wherein an inner surface of the flow restriction feature includes a surface treatment that generates at least one of rotation and turbulence in a cleaning fluid flowing through the flow restriction feature.

6. The method of claim 1, wherein the tube outlet ends are arranged in rows, and further comprising:
   disposing a first row of deposition pins in a row of tube outlet ends, each tube outlet end of the row receiving no more than one deposition pin of the first row of deposition pins;
   removing the first row of deposition pins from the row of tube outlet ends; and
   subsequent to removing the first row of deposition pins from the row of tube outlet ends, disposing a second row of deposition pins in the row of tube outlet ends, each tube outlet end of the row receiving no more than one deposition pin of the second row of deposition pins.

7. The method of claim 1, wherein a plurality of pins are disposed in a plurality of tubes on a one-for-one basis, and wherein the tube outlet ends are above a level of cleaning fluid such that each of the plurality of pins is washed within a respective cleaning tube, and wherein the cleaning fluid passes each tube and exits at outlet ends such that the fluid that cleans a first pin is drained and does not come into fluid contact with a second pin.

8. The method of claim 1, wherein the vent tube outlet end includes a portion directed away from the cleaning tube outlet ends.

9. The method of claim 1, wherein the vent tube outlet end includes a surface tension reduction feature disposed within the vent tube for reducing surface tension of fluid within the vent tube.

10. The method of claim 9 wherein the surface tension reduction feature includes a wire disposed within the vent tube.

11. The method of claim 9, wherein the surface tension reduction feature is a notch in a lip of at least one of the tube outlet ends.

12. The method of claim 9, wherein the surface tension reduction feature includes a surface finish on an outside surface of at least one of the tube outlet ends.

13. The method of claim 12, wherein the surface finish includes at least one of a bead blasting treatment, a grit blasting treatment, a hydrophilic treatment, and a hydrophobic treatment.

14. The method of claim 1, wherein the substantially horizontal reference plane corresponds to a level of a cleaning fluid in the lower chamber.

15. The method of claim 1, wherein at least one of the plurality of cleaning tube outlet ends has a fluid surface tension reduction feature.

* * * * *